(12) United States Patent
Osanai et al.

(10) Patent No.: US 10,959,608 B2
(45) Date of Patent: Mar. 30, 2021

(54) OPTICAL IMAGING DEVICE

(71) Applicant: TOHOKU UNIVERSITY, Miyagi (JP)

(72) Inventors: Makoto Osanai, Miyagi (JP); Hajime Mushiake, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 230 days.

(21) Appl. No.: 16/089,662

(22) PCT Filed: Mar. 29, 2017

(86) PCT No.: PCT/JP2017/012850
§ 371 (c)(1),
(2) Date: Sep. 28, 2018

(87) PCT Pub. No.: WO2017/170662
PCT Pub. Date: Oct. 5, 2017

(65) Prior Publication Data
US 2020/0305697 A1    Oct. 1, 2020

(30) Foreign Application Priority Data
Mar. 31, 2016  (JP) .............................. JP2016-071769

(51) Int. Cl.
*A61B 1/045* (2006.01)
*G02B 23/26* (2006.01)

(52) U.S. Cl.
CPC .............. *A61B 1/045* (2013.01); *G02B 23/26* (2013.01)

(58) Field of Classification Search
None
See application file for complete search history.

(56) References Cited

U.S. PATENT DOCUMENTS

| 4,618,884 A | 10/1986 | Nagasaki |
| 2005/0207668 A1 | 9/2005 | Perchant et al. |

(Continued)

FOREIGN PATENT DOCUMENTS

| CN | 101375786 | 3/2009 |
| JP | 60-53919 | 3/1985 |

(Continued)

OTHER PUBLICATIONS

International Search Report dated Jun. 27, 2017 in International (PCT) Application No. PCT/JP2017/012850.

(Continued)

*Primary Examiner* — Eileen M Adams
(74) *Attorney, Agent, or Firm* — Wenderoth, Lind & Ponack, L.L.P.

(57) ABSTRACT

Provided is a fluorescence imaging device comprising: a light source for irradiating a subject with a laser for exciting a fluorescent dye; a condensing lens that receives light from the light source, an endoscopic probe comprising an image fiber and a lens that is disposed on the distal end of the image fiber; a photodetector that detects return light from the subject; and an oscillating element that is connected to the image fiber or the condensing lens and that, upon application of a voltage, causes the image fiber or the condensing lens to oscillate. With this configuration, a lattice pattern of fiber elements, which appears in an image of a subject, can be cancelled in real time by oscillating the oscillating element.

5 Claims, 7 Drawing Sheets

(56) References Cited

U.S. PATENT DOCUMENTS

| | | | |
|---|---|---|---|
| 2006/0089554 A1* | 4/2006 | Ishihara | A61B 5/0071 600/476 |
| 2010/0317923 A1 | 12/2010 | Endo et al. | |
| 2011/0128532 A1* | 6/2011 | Taira | G02B 21/0076 356/218 |
| 2015/0160168 A1* | 6/2015 | Irisawa | F21V 13/02 73/645 |
| 2017/0045734 A1 | 2/2017 | Shimamoto | |
| 2017/0071455 A1 | 3/2017 | Shimamoto | |

FOREIGN PATENT DOCUMENTS

| | | |
|---|---|---|
| JP | 63-265215 | 11/1988 |
| JP | 2005-160815 | 6/2005 |
| JP | 2005-532884 | 11/2005 |
| JP | 2006-3747 | 1/2006 |
| JP | 2010-284369 | 12/2010 |
| JP | 2013-17768 | 1/2013 |
| JP | 2015-128548 | 7/2015 |
| JP | 2015-139537 | 8/2015 |
| WO | 2012/082789 | 6/2012 |
| WO | 2015/125976 | 8/2015 |
| WO | 2015/182139 | 12/2015 |

OTHER PUBLICATIONS

Makoto Osanai et al., "Development of a micro-imaging probe for functional brain imaging", Neuroscience Research, 2013, vol. 75, pp. 46-52.

Notice of Reasons for Refusal dated Jan. 19, 2021 in corresponding Japanese Patent Application No. 2018-508134, with Machine Translation.

* cited by examiner

OPTICAL IMAGING DEVICE

TECHNICAL FIELD

The present invention relates to an optical imaging device.

BACKGROUND ART

An image fiber composed of a bundle of optical fibers is used for an endoscopic probe, which is an image transmission portion of an optical imaging device. Since an image fiber with a small number of pixels must be used for small-diameter endoscopes that enable a cellular level of observation, the lattice pattern of individual fiber elements affects visibility.

To reduce the lattice pattern of fiber elements, Patent Literature (PTL) 1 discloses a fluorescence imaging device that processes an acquired image using software to smooth the image, thus making this lattice pattern less visible and making the image of an object more visible.

Patent Literature (PTL) 2 discloses an observation and/or imaging device for endoscopes, which comprises a transparent plate accommodated in a frame body between a lens and an image guide in an endoscope, and piezoelectric oscillators that are fixed to the frame body and in contact with 4 portions of the transparent plate, which are on the upper, lower, right, and left peripheral edges of the transparent plate, whereby the fiber displacement pattern is removed by vibrating the piezoelectric vibrators.

Patent Literature (PTL) 3 discloses an endoscopic system having a shift mechanism, which causes a piezoelectric element formed on the outer periphery of an incident end of an image guide to oscillate the incident end of an image guide and periodically shifts the incident end of the image guide relative to the image formed by an objective optical system.

CITATION LIST

Patent Literature

PTL 1: JP2005-532884A
PTL 2: JPS60-53919A
PTL 3: JP2010-284369A

SUMMARY OF INVENTION

Technical Problem

However, the smoothing treatment using software disclosed in PLT 1 fails to obtain an image compensated by smoothing in real time. Furthermore, the processing using software is applicable only to fluorescence imaging devices with dedicated software, and thus has poor versatility and is expensive.

The device disclosed in PTL 2 has a complicated structure because the piezoelectric oscillators are fixed between a lens and an image guide in an optical path and the device also has a problem in that it can only exhibit a poor effect of removing a fiber pattern at the fiber end on the detection-side due to the deformation of light incident on fibers constituting an image guide.

In PTL 3, the shift mechanism using a piezoelectric element is shifted in accordance with the CCD frame rate to capture the image of an object several times per shift cycle and the obtained multiple frame images are synthesized into a single synthetic image. Thus, the image cannot be obtained in real time. Furthermore, since the shift mechanism is located on the tip of an image guide on a subject side, the endoscopic system of PTL 3 has a poor effect of removing a lattice pattern of the image guide observed by a CCD camera.

An object of the present invention is to provide an optical imaging device capable of cancelling, in real time, a lattice pattern of fiber elements, which appears in the image of a subject.

Solution to Problem

To achieve the above object, the present inventors found that when an oscillating element is attached to an endoscopic probe and the fiber is oscillated at a high speed, images can be smoothed in real time with a simple mechanical structure. The present invention has been accomplished based on this finding.

According to a first embodiment of the present invention, the present invention provides a fluorescence imaging device comprising: a light source for irradiating a subject with light; a condensing lens that receives light from the light source; an endoscopic probe comprising an image fiber and a lens disposed on the distal end side of the image fiber, the image fiber being composed of a bundle of optical fibers, the fibers guiding to the subject the light from the light source that is incident through the condensing lens; a photodetector that detects return light from the subject; and an oscillating element that is connected to the image fiber, the condensing lens, or the photodetector and that causes the image fiber, the condensing lens, or the photodetector to oscillate.

In another embodiment, the optical imaging device further comprises a display device for displaying an image of a subject produced from return light detected with the photodetector.

In another embodiment, the oscillating element operates so as to cancel a lattice pattern of fiber elements of the image fiber in an image of a subject obtained from the photodetector.

In another embodiment, the lens disposed on the distal end side of the image fiber is a GRIN lens coupled to the tip of the image fiber.

A second embodiment of the present invention provides a method for processing an image of a subject by using an optical imaging device, the device comprising a light source for irradiating a subject with light; a condensing lens that receives light from the light source; an endoscopic probe comprising an image fiber and a lens disposed on the distal end side of the image fiber, the image fiber being composed of a bundle of optical fibers, the fibers guiding to a subject the light from the light source that is incident through the condensing lens; a photodetector that detects return light from a subject; and an oscillating element connected to the image fiber or the condensing lens, the method comprising oscillating the oscillating element so as to cancel a lattice pattern of fiber elements of the image fiber in the image of the subject.

In one embodiment, the oscillating element is oscillated in real time during a display of the image.

Advantageous Effects of Invention

According to the present invention, a compensated clear image can be obtained in real time. Moreover, image compensation can be performed at low cost. Furthermore, the

DESCRIPTION OF EMBODIMENTS

A first embodiment of the present invention embodied in a fluorescence imaging device is described below with reference to the drawings.

Figure 1:
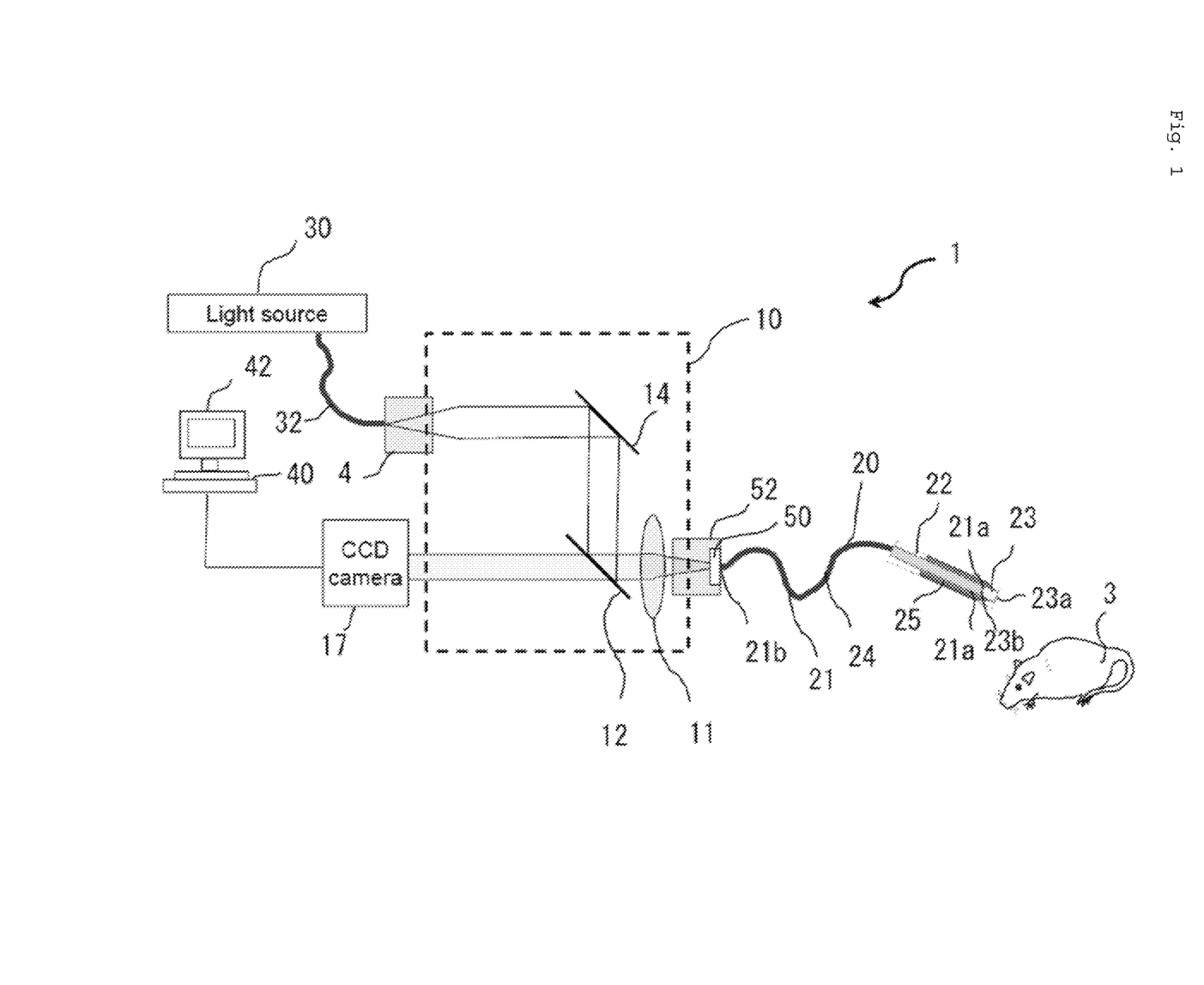
FIG. 1 is a schematic illustration of the fluorescence imaging device according to a first embodiment of the present invention.

The fluorescence imaging device 1 according to the first embodiment of the present invention comprises an optical system 10; a CCD camera 17 that is detachably connected to the optical system 10 and that functions as a photodetector for detecting return light from a subject 3; an endoscopic probe 20 that is detachably connected to the optical system 10 and that microscopically observes the subject 3; a light source 30 that is detachably connected to the optical system 10 and that is for irradiating a subject 3 with a laser for exciting a fluorescent dye; and a personal computer 40 that is detachably connected to the optical system 10.

The optical system 10 receives light from the light source 30 and transmits the light to a subject 3, and also transmits light from the endoscopic probe 20 to the CCD camera 17. The subject 3 may be an animal, a plant, a microorganism; tissues thereof; or cells thereof. Fluorescence in the subject 3 is expressed either by a fluorophore administered to the subject 3 by injection or the like, such as a fluorescent dye for intracellular imaging, or by a fluorophore produced by the subject 3. The fluorescence can be observed by irradiation with a laser for exciting a fluorescent dye from the light source 30. The personal computer 40 comprises a monitor 42, which functions as a display device for displaying a produced image of the subject 3.

The distal end of the optical fiber 32 of the light source 30 is connected to a connector 4 provided on a unit of the optical system 10 to thereby connect the light source 30 to the optical system 10. Further, the proximal end of the optical fiber 21 of the endoscopic probe 20 is connected to a retaining member 52 for connecting the image fiber 21, the retaining member 52 being provided on the unit of the optical system 10, to thereby connect the endoscopic probe 20 to the optical system 10.

The optical system 10 comprises a condensing lens 11 disposed in response to the endoscopic probe 20; a mirror 12 that receives light from the light source 30 and reflects the light to the condensing lens 11; and a mirror 14 that receives excitation light from the light source 30 and reflects a portion of the light to the mirror 12.

The return light from the endoscopic probe 20 is received by a CCD camera 17. The signal that is A/D converted by the CCD camera 17 is input to a personal computer 40. The personal computer 40 generates two-dimensional image data.

The image data stored in the memory of the personal computer 40 is, for example, D/A converted to, for example, a standard video signal, and output to a monitor 42 of the personal computer 40. The monitor 42 displays an image of tissues or cells of the subject 3.

Figure 2A:
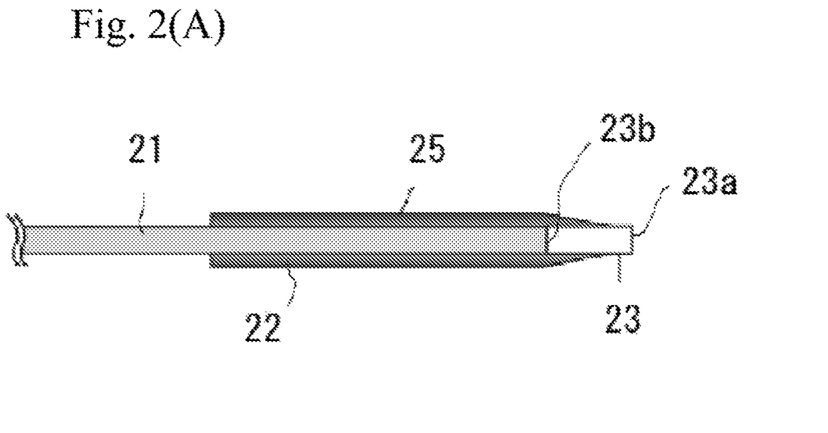
FIG. 2(A) is a partially enlarged view of the endoscopic probe of FIG. 1.
Figure 2B:
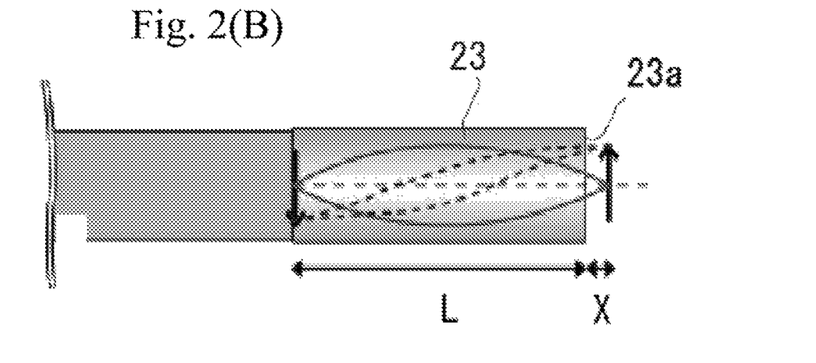
FIG. 2(B) is an enlarged view of the distal end portion of FIG. 2(A).

Next, the endoscopic probe 20 is described in more detail. With reference to FIG. 1, FIG. 2(A), and FIG. 2(B), the endoscopic probe 20 comprises an image fiber 21 comprising a bundle of fibers (also referred to as fiber elements), which guide the light incident through a condensing lens 11 from a light source 30; and an optical head 22 connected to the distal end side of the image fiber 21. The optical head 22 comprises a lens 23 that produces an optical image of return light from the subject 3 on the distal end face of the image fiber 21. Although the number of pixels of the image fiber 21 is not particularly limited, it is usually from 5000 to 100000, for example, about 10000. A substantial portion of the length of the image fiber 21 from the proximal end of the image fiber 21 is covered with a flexible material 24, and the proximal end portion of the optical head 22 (lens 23) is covered with a sheath 25. The sheath 25 can be formed of a metal, a resin, or a combination thereof. A tube 26 made of a metal or the like for holding the endoscopic probe 20 (see FIG. 3) may be further provided on the sheath 25.

With this configuration, the endoscopic probe 20 guides light from a light source 30, i.e., light incident from the optical system 10, to the subject 3 through the image fiber 21 and the lens 23, and also transmits return light from the subject 3 to the condensing lens 11 through the lens 23 and the image fiber 21.

The lens 23 does not necessarily have to be directly connected to the tip 21a of the image fiber 21. It is sufficient if the lens 23 is disposed near the tip 21a of the image fiber 21 so as to transmit light incident from the tip 21a of the image fiber 21. FIG. 2 shows a configuration in which the proximal end 23b of the lens 23 is connected to the tip 21a of the image fiber 21 and the distal end portion of the image fiber 21 and the proximal end portion of the lens 23 are substantially in line with each other.

The lens 23 may be any lens that can condense light led from the image fiber 21. Examples of such lenses include conventional optical lenses and gradient refractive index lenses (GRIN lenses). Among these, GRIN lenses are preferable because they have a thin diameter and fine regions of the subject 3 can be observed with such lenses. The optical head 22 (lens 23) is either brought into contact with the surface of the subject 3, or pierced into the subject 3. The excitation laser emitted from the light source 30 is focused on a spot at a depth of several tens of micrometers to several hundreds of micrometers from the surface.

With reference to the example of a GRIN lens shown in FIG. 2(B), the GRIN lens has a length L of 2.5 mm and a diameter of 350 µm; the distance X from the front end 23a of the lens 23 to a focal plane is approximately 100 µm.

Figure 4A:
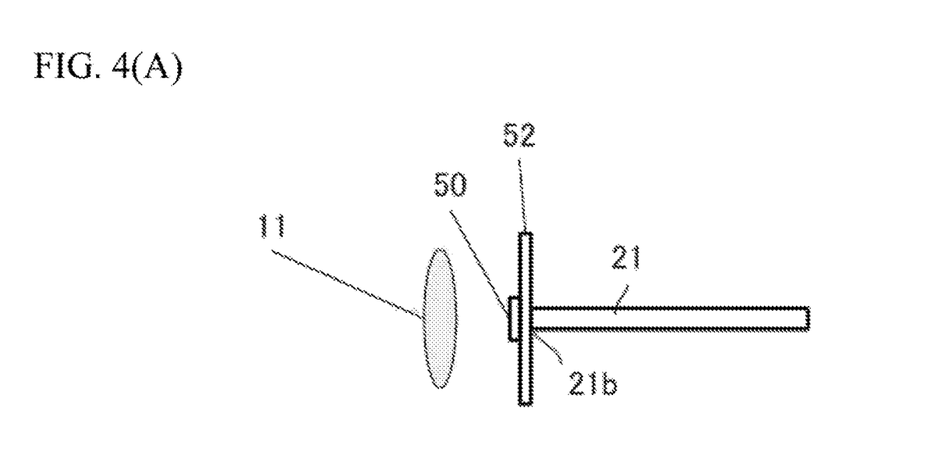
FIG. 4(A) is a partially enlarged side view showing the attachment of an oscillating element.
Figure 4B:
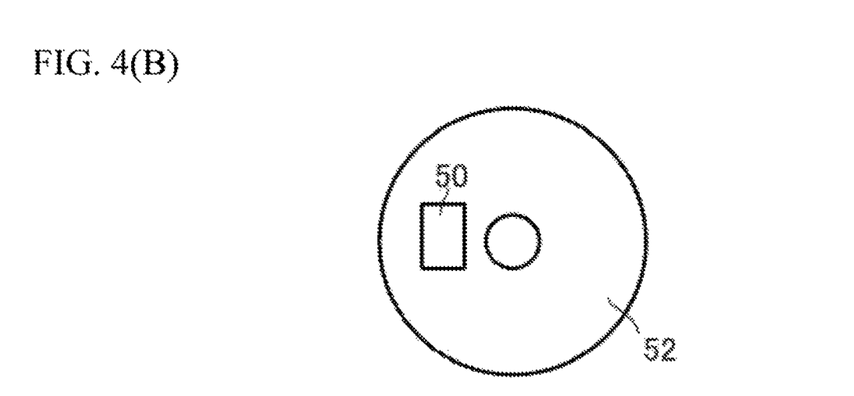
FIG. 4(B) is a view of the end face.

In this embodiment, the fluorescence imaging device 1 is connected to the proximal end 21b of the image fiber 21 through a connector 5 (see FIG. 4(A) and FIG. 4(B)) and is provided with one or more oscillating elements 50 that, upon application of a voltage, cause the image fiber 21 to oscillate. Examples of oscillating elements 50 include linear actuators (linear motors), piezoelectric elements, magnetostrictive elements, crystal oscillators, ultrasonic oscillating elements, and the like. Commercially available oscillating elements can be used as the oscillating element 50.

FIG. 4(A) and FIG. 4(B) show the displacement of the oscillating element 50. The proximal end 21b of the image fiber 21 is connected to a connector 5, and the connector 5 is attached to a retaining member 52 for holding the connector 5. The retaining member 52 is fixed to the optical system 10. In this example, the oscillating element 50 is disposed between the proximal end 21b of the image fiber 21 and the condensing lens 11. Specifically, the oscillating element 50 is attached to a face of the retaining member 52 opposite to that to which the proximal end 21b of the image fiber 21 is connected.

With reference back to FIG. 1, during fluorescence observation, a voltage is applied to the oscillating element 50 to oscillate the oscillating element 50 in such a manner as to oscillate the image fiber 21, whereby a lattice pattern of fiber elements of the image fiber 21 in an image of the subject 3 can be cancelled, the image being obtained from the signal obtained from the CCD camera 17 and displayed on the monitor 42.

The rate of oscillation of the oscillating element 50 at which the lattice pattern of fiber elements is cancelled is preferably faster than the rate at which the CCD camera 17 captures an image. With respect to the magnitude of oscillation of the oscillating element 50 at which a lattice pattern of fiber elements can be cancelled, a person skilled in the art can be easily set such a magnitude of oscillation by changing the level of voltage applied and maintaining the voltage with the lattice pattern on the monitor 42 being cancelled. Without wishing to be bound to any particular theory, a more remarkable effect of cancelling the lattice pattern of fiber elements is considered to be obtained by setting the magnitude of oscillation in such a manner that the moving distance of the oscillating element 50 by oscillation is one half or more of the distance between the centers of adjacent fiber elements. Since oscillation of the oscillating element 50 can be performed in real time at any time during the observation of a subject 3, such as capturing, production, or display of an image of a subject 3, the image of a subject 3 displayed on the monitor 42 is an image compensated by oscillation, and no time lag for image compensation occurs. According to this embodiment, the image produced by a personal computer 40 does not have to be subjected to software post-processing using an image smoothing filter, such as a Gaussian filter, and the image can be smoothened in real time by a simple mechanical structure. "Cancelling the lattice pattern of fiber elements" herein means that the lattice pattern is reduced, as compared with an image obtained without using the oscillating element 50; it includes reduction of the lattice pattern to a level invisible to the observer.

The present invention is explained above with reference to the first embodiment as an example. However, the present invention is not limited to the first embodiment and can be modified in various ways, for example, as follows.

The structure of the optical system 10 is not limited to that of the first embodiment. The optical system 10 may have any optical system structure that can be understood by persons skilled in the art. For example, a part of the constituent elements according to the first embodiment may be omitted from the optical system 10, or the optical system 10 may further comprise one or more lenses, filters, and/or mirrors.

The CCD camera 17 may be other imaging elements, such as a CMOS camera or a photodiode array.

Lens 23 may be omitted.

The sheath 25 may be formed of a metal or any other material, such as resin or ceramics. The sheath 25 may be omitted.

The light source 30 may be a light source for transmitted light observation, in place of a light source for fluorescence observation. The light source 30 may be a laser light source, or other light source, such as a xenon lamp, mercury lamp, or halogen lamp. That is, the present invention may be embodied in an optical imaging device provided with a light source for irradiating a subject with light.

The light source 30 may be directly bound to the optical system 10, not through an optical fiber 32.

In place of the personal computer 40, other image processing devices may be used.

In FIG. 4, one oscillating element 50 is disposed horizontally at the same height as that of the proximal end 21b of the image fiber 21. However, the oscillating element 50 may be provided at an upper-side or lower-side position with respect to the proximal end 21b of the image fiber 21. The number of oscillating elements 50 is also not limited to one, and may be 2, 3, 4, or more.

In the first embodiment, the oscillating element 50 is connected to the proximal end 21b of the image fiber 21 through the retaining member 52. However, as long as the oscillating element 50 oscillates the connector 5 or the image fiber 21 with respect to the optical axis of the condensing lens 11, the effect of cancelling the lattice pattern of fiber elements of the image fiber 21 is obtained. Therefore, the oscillating element 50 may be attached to a position other than that of the first embodiment on the retaining member 52, or to the image fiber 21, condensing lens 11, or CCD camera 17. When the oscillating element 50 is attached to the image fiber 21, the oscillating element 50 may be attached to, for example, a position within 0 to 5 cm from the proximal end 21b of the proximal end portion of the image fiber 21. Further, when the oscillating element 50 is connected to the image fiber 21, the condensing lens 11, or the CCD camera 17, the connection includes not only direct connection but also indirect connection via other member(s). It is sufficient as long as the oscillating element 50 is directly or indirectly connected to the image fiber 21, the condensing lens 11, or the CCD camera 17 and can cause the image fiber image to oscillate relative to the optical axis of the CCD camera 17.

In the first embodiment, explanation was made by using an optical system 10 of a vertical illumination-type fluorescence microscope as the optical system. Alternatively, the optical system in the fluorescence imaging device of the present invention may be an optical system of a confocal laser scanning microscope.

Even when the magnitude of oscillation is such that the moving distance of the oscillating element 50 by oscillation is less than one half of the distance between adjacent fiber elements, it is included within the scope of the present invention, as long as the lattice pattern is reduced.

The present invention further includes a method for processing an image of a subject by using an optional imaging device, the device comprising:
a light source 30 for irradiating a subject 3 with light; a condensing lens 11 that receives light from the light source 30;
an endoscopic probe comprising an image fiber comprising an image fiber 21 and a lens 22 that is disposed on the distal end side of the image fiber 21, the image fiber being composed of a bundle of fibers, the fibers guiding to a subject the light from the light source 30 that is incident through the condensing lens; a photodetector 17 that detects return light from the subject; and an oscillating element 50 connected to the image fiber 21 or the condensing lens 11,
the method comprising oscillating the oscillating element 50 in such a manner that a lattice pattern of fiber elements of the image fiber 21 in the image of the subject 3 is cancelled.

The present invention is more specifically described below with reference to Examples. However, the present invention is not limited to these Examples.

EXAMPLES

Example 1

Production Example of Fluorescence Imaging Device 1.1 Preparation of Optical System of Fluorescence Imaging Device A unit of an optical system 10 having the structure shown in FIG. 1 was produced as a trial product using a known optical system. The size of this trial product is within a square with a side length of 30 cm. As compared with a stationary microscope device, this trial product is compact and has excellent portability.

1.2 Preparation of Endoscopic Probe

Figure 3:
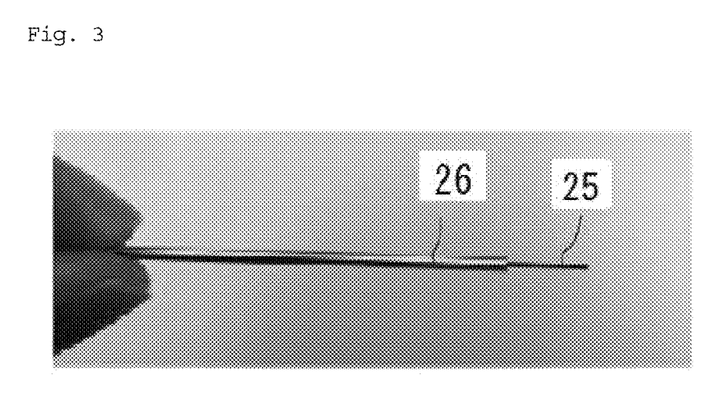
FIG. 3 is a trial product of an endoscopic probe.

An image fiber of 10,000 pixels and a GRIN lens with a diameter of 350 μm were connected according to the disclosure of Osanai et al., Neuroscience research 75: 46-52, 2013 to produce a trial product of an endoscopic probe 20 having the same structure as shown in FIG. 2. FIG. 3 is a photograph of the trial product.

1.3 Installation of Oscillating Element

As shown in FIG. 4(A) and FIG. 4(B), an oscillating element 50 was attached to the proximal end of an image fiber 21 so as to be adjacent to an objective lens (condensing lens 11). As the oscillating element 50, a linear vibration actuator was used. To observe one portion of a subject 3 with an endoscopic probe 20, one image fiber 21 was prepared.

1.4 Comparison of the Fluorescence Imaging Device of the Present Invention and the Fluorescence Imaging Device of the Prior Art The fluorescence imaging device of the present invention was completed by further connecting, to the unit of the optical system 10 explained above in 1.1, a light source 30 for irradiating a subject 3 with a laser for exciting a fluorescent dye, a CCD camera 17, and a monitor 42.

The performance of the fluorescence imaging device of the present invention was compared with that of an endoscopic fluorescence imaging device of the prior art in which a lattice pattern of fiber elements is processed using software (Table 1). The fluorescence imaging device of the present invention is advantageous over the conventional fluorescence imaging device in that it can select the wavelength of the light source, can extend the optical system, and is low-cost.

TABLE 1

| Characteristics | The System of the Present Invention | Fluorescence Imaging Device of the Prior Art | Relative Merits |
|---|---|---|---|
| Excitation wavelength | Freely selectable | Fixed (only at a constant wavelength) | ++ |
| Fluorescence wavelength | Freely selectable | Fixed (The fluorescent dye-specific fluorescence acquisition capacity is low due to its wide band) | ++ |
| Optical system | The maximum use of the advantages of the image fiber can be made when used when the device is used as an epifluorescent microscope; stimulation light can be additionally introduced | Confocal system. The optical system cannot be extended. | +++ |
| Software | Freely selectable | Only dedicated software can be used. | + |
| Cost | Inexpensive (about 5 million yen) | Expensive (several tens of millions of yen) | ++ |
| Application range | A wide range of application, such as optogenetics and microsurgery | Imaging alone | |

Example 2

Figure 5:
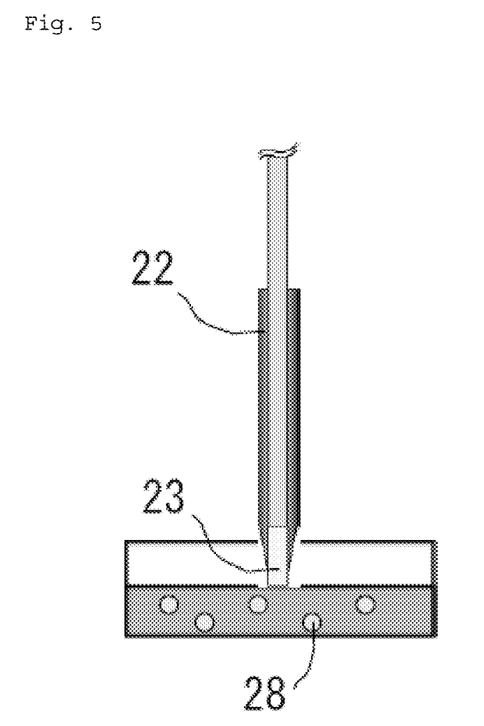
FIG. 5 is a schematic diagram illustrating the application of the endoscopic probe of the trial product to a petri dish containing 4-μm fluorescent beads.

Fluorescence Observation Using 4-μm Fluorescent Beads and Effect as a Canceler of the Lattice Pattern of Fiber Elements of the Oscillating Element Fluorescent beads with a diameter of 4 μm (TetraSpeck, Invitrogen, reference symbol 28 in FIG. 8) were mixed with a 1% agarose solution and gelled at room temperature. An endoscopic probe was pierced into this agarose gel and irradiated with excitation light with a wavelength of 473 nm. Fluorescence was observed using the fluorescence imaging device of Example 1 (FIG. 5).

Figure 6A:
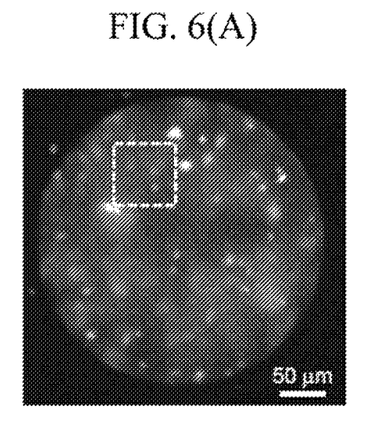
FIG. 6(A) is an image of fluorescent beads with a diameter of 4 μm before operation of the oscillating element.
Figure 6B:
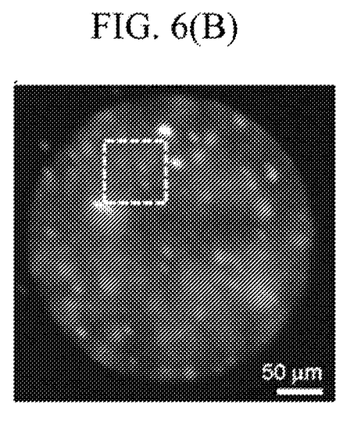
FIG. 6(B) is an image of the fluorescent beads of FIG. 6(A) during the operation of the oscillating element.
Figure 6C:
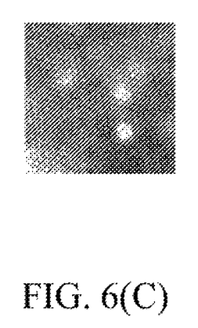
FIG. 6(C) is an enlarged view of the dotted line rectangle portion of FIG. 6(A).
Figure 6D:
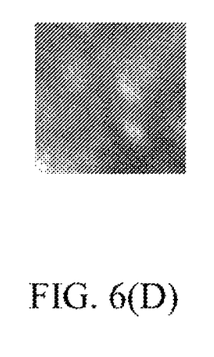
FIG. 6(D) is an enlarged view of the dotted line rectangle portion of FIG. 6(B).

Before the operation of the oscillating element, as shown in FIG. 6(A) and FIG. 6(C), the lattice pattern of fiber elements was observed around beads. Voltage was applied to the oscillating element of the fluorescence imaging device of Example 1 so as to oscillate the image fiber. When the voltage had reached a certain level, cancellation of a lattice pattern of the fiber elements on the monitor 42 was observed with the naked eye (FIG. 6(B) and FIG. 6(D)), and a clearer image of the beads was obtained in real time.

The FWHM of the fluorescence intensity profile in the observation of fluorescent beads with a diameter of 4 μm was about 5 μm before oscillation by the oscillating element 50, and was about 8 μm after the oscillation. Since the difference between these was about 3 μm, resolution in the x-y directions was proven to be a spatial resolution sufficient for observing cells even after the oscillation.

Example 3

Observation of Cerebral Cortex GABA Neuron (GAD67-KI Mouse)

Figure 7:
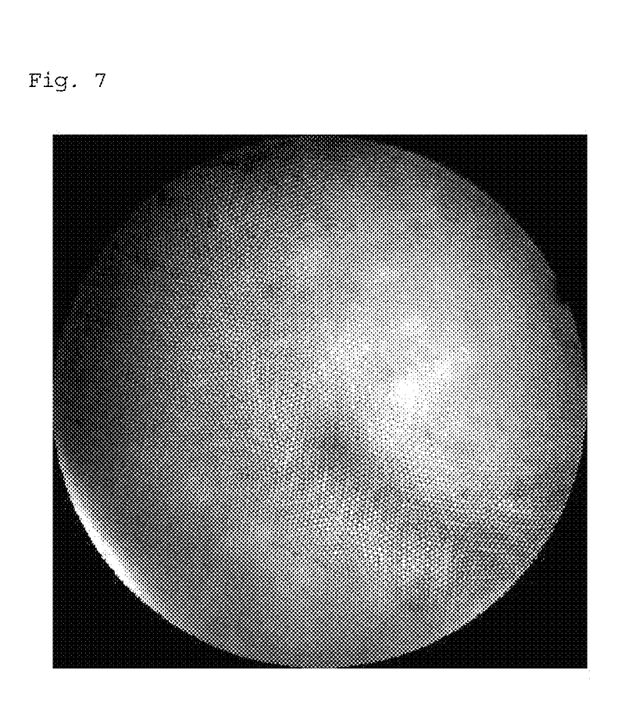
FIG. 7 is a fluorescence image of inhibitory neurons of the cerebral cortex expressing GFP (GABA neuron).

Using the fluorescence imaging device of Example 1, a cerebral cortex GABA neuron (GAD67-KI mouse) expressing green fluorescent protein (GFP) was observed by piercing the endoscopic probe into the cerebral cortex GABA neuron. Single cells were sufficiently visualized, but a lattice pattern of fiber elements was observed in its raw image (FIG. 7).

When the fluorescence imaging device of the present invention is used, the lattice pattern of fiber wires can be cancelled by the piezoelectric element 50.

The embodiments of the present invention and Examples are specifically described above. However, the present invention is not limited to the above embodiments, and various modifications based on the technical idea of the present invention can be made.

Further, the present invention can also have the following structures.

(1) A fluorescence imaging device comprising: a light source for irradiating a subject with light; a condensing lens that receives light from the light source; an endoscopic probe an endoscopic probe comprising an image fiber and a lens that is disposed on the distal end side of the image fiber, the image fiber being composed of a bundle of fibers, the fibers guiding to the subject the light from the light source that is incident through the condensing lens; a photodetector that detects return light from the subject; and an oscillating element connected to the image fiber, the condensing lens, or the photodetector so as to cause the image fiber, the condensing lens, or photodetector to oscillate.

(2) The optical imaging device according to (1), further comprising a display device for displaying an image of a subject produced from return light detected by the photodetector.

(3) The optical imaging device according to (2), wherein the oscillating element operates so as to cancel a lattice pattern of fiber elements of the image fiber in an image of a subject obtained from the photodetector.

(4) The optical imaging device according to (1), wherein the lens disposed on the distal end of the image fiber is a GRIN lens coupled to the distal end of the image fiber.

(5) The optical imaging device according to any one of (1) to (4), wherein the light source is a light source for fluorescence observation.

(6) The optical imaging device according to any one of (1) to (5), wherein the oscillating element is directly or indirectly connected to the proximal end portion of the image fiber.

(7) A method for processing an image of a subject by using an optical imaging device, the device comprising a light source for irradiating a subject with light; a condensing lens that receives light from the light source; an endoscopic probe comprising an image fiber and a lens that is disposed on the distal end side of the image fiber, the image fiber being composed of a bundle of fibers, the fibers guiding to the subject the light from the light source that is incident through the condensing lens; a photodetector for detecting return light from the subject; and an oscillating element connected to the image fiber or the condensing lens, and the method comprising oscillating the oscillating element in such a manner that a lattice pattern of fiber elements of the image fiber in the image of the subject is cancelled.

(8) The method according to (7), wherein the oscillating element is oscillated in real time during a display of the image.

INDUSTRIAL APPLICABILITY

The optical imaging device of the present invention is low-cost and is applicable to conventional optical imaging devices. Therefore, the optical imaging device of the present invention can be widely used in various fields, such as medical science and analysis, in which fluorescence observation of a subject is required. For example, the optical imaging device of the present invention can be used for a living body deep portion imaging fluorescence endoscope system for basic research, a minimally invasive endoscope system for clinical application, and a superfine endoscope system for non-destructive testing.

The invention claimed is:

1. An optical imaging device comprising:
   a light source for irradiating a subject with light;
   a condensing lens that receives light from the light source;
   an endoscopic probe comprising an image fiber and a lens that is disposed on the distal end side of the image fiber, the image fiber being composed of a bundle of fibers, the fibers guiding to the subject the light from the light source that is incident through the condensing lens;
   a photodetector that detects return light from the subject; and
   an oscillating element that is connected to the image fiber, the condensing lens, or the photodetector and causes the image fiber, the condensing lens, or the photodetector to oscillate wherein the oscillating element operates so as to cancel a lattice pattern of fiber elements of the image fiber in an image of a subject obtained from the photodetector.

2. The optical imaging device according to claim 1, further comprising a display device for displaying an image of a subject produced from return light detected by the photodetector.

3. An optical imaging device comprising:
   a light source for irradiating a subject with light;
   a condensing lens that receives light from the light source;
   an endoscopic probe comprising an image fiber and a lens that is disposed on the distal end side of the image fiber, the image fiber being composed of a bundle of fibers, the fibers guiding to the subject the light from the light source that is incident through the condensing lens;
   a photodetector that detects return light from the subject; and
   a vibrating element that is connected to the image fiber, the condensing lens, or the photodetector and causes the image fiber, the condensing lens, or the photodetector to oscillate wherein the lens disposed on the distal end side of the image fiber is a GRIN lens coupled to the tip of the image fiber.

4. A method for processing an image of a subject by using an optical imaging device, the device comprising:
   a light source for irradiating a subject with light;
   a condensing lens that receives light from the light source;
   an endoscopic probe comprising an image fiber and a lens that is disposed on the distal end side of the image fiber, the image fiber being composed of a bundle of fibers, the fibers guiding to the subject the light from the light source that is incident through the condensing lens;

a photodetector for detecting return light from the subject; and an oscillating element connected to the image fiber or the condensing lens, the method comprising oscillating the oscillating element in such a manner that a lattice pattern of fiber elements of the image fiber in the image of the subject is cancelled.

5. The method according to claim 4, wherein the oscillating element is oscillated in real time during a display of the image.

\* \* \* \* \*